United States Patent [19]

Akiyama et al.

[11] 4,220,802

[45] * Sep. 2, 1980

[54] PROCESS FOR THE PREPARATION OF ACRYLIC ACID

[75] Inventors: Shinichi Akiyama; Haruhisa Yamamoto, both of Takaoka, Japan

[73] Assignee: Nippon Zeon Co. Ltd., Tokyo, Japan

[*] Notice: The portion of the term of this patent subsequent to Feb. 21, 1995, has been disclaimed.

[21] Appl. No.: 848,668

[22] Filed: Nov. 4, 1977

Related U.S. Application Data

[63] Continuation of Ser. No. 597,163, Jul. 18, 1975, abandoned.

[30] Foreign Application Priority Data

Jul. 26, 1974 [JP] Japan ................................. 49-85763

[51] Int. Cl.² ........................ C07C 51/32; C07C 57/04
[52] U.S. Cl. .................................. 562/535; 252/432; 252/435; 252/437
[58] Field of Search .................. 260/530 N; 252/435, 252/437, 432; 562/535

[56] References Cited

U.S. PATENT DOCUMENTS

| | | | |
|---|---|---|---|
| 3,795,703 | 3/1974 | Niina et al. | 260/530 N |
| 3,865,873 | 2/1975 | Oda et al. | 562/535 |
| 3,875,220 | 4/1975 | White et al. | 260/530 N |
| 3,998,877 | 12/1976 | Oda et al. | 562/535 |
| 4,075,244 | 2/1978 | Akiyama et al. | 562/535 |

*Primary Examiner*—Vivian Garner
*Attorney, Agent, or Firm*—Sherman & Shalloway

[57] ABSTRACT

A process for the preparation of acrylic acid which comprises reacting acrolein with molecular oxygen in the vapor phase in the presence of an oxidation catalyst composition having the following empirical formula $$Mo_aP_bV_cL_dM_eO_f$$

wherein L is at least one element selected from the group consisting of Rb, Cs and K; M is at least one element selected from the group consisting of Sr, Nb, Cd, B, Zn and Pb; and a, b, c, d, e and f each represent the number of atoms of each element; the atomic ratio of a:b:c:d:e being 12:0.1–8:0.1–8:0.1–8:0–6; and f being the number of oxygen atoms determined by the valence requirement of the other elements present; and an oxidation catalyst used therefor.

14 Claims, No Drawings

PROCESS FOR THE PREPARATION OF ACRYLIC ACID

This is a continuation of application Ser. No. 597,163, filed July 18, 1975, now abandoned.

This invention relates to a process for preparing acrylic acid by the vapor phase oxidation of acrolein, using a specific catalyst which not only excels in its catalytic activity (namely, the property of providing acrylic acid in good yield at a high selectivity and productivity) but also possesses a long active life.

The process by which acrylic acid is prepared using as the starting material acrolein obtained by the vapor phase oxidation of propylene has been the subject of investigation of many researchers, because this process makes it possible to produce acrylic acid commercially at low cost. Hence, numerous patent gazettes and research reports have been published concerning this process.

These patent gazettes and research reports are principally directed to a process for obtaining acrylic acid by the vapor phase oxidation of acrolein with a molecular oxygen such as air in the presence of a catalyst. According to these patent gazettes and research reports, good results seem to be demonstrated by the Mo-V type catalysts which contain molybdenum, vanadium and oxygen. For example, it is mentioned in British Pat. No. 903,034 and Japanese Patent Publication No. 1775/66 that excellent results are had by the use of the Mo-V type catalysts, while in Japanese Patent Publications Nos. 16604/67, 30698/70 and 37561/71 there is mentioned that superior results are obtained by the use of Mo-V-As type catalysts. On the other hand, Japanese Patent Publication No. 13092/73 and Japanese Laid-Open Application No. 92321/73 report that excellent results are demonstrated by the use of Mo-V-Fe type catalysts.

However, the Mo-V type catalysts are known to possess such drawbacks as that their reproducibility is poor and that the change in catalytic activity with the passage of time is great (see Japanese Patent Publication No. 13092/73). In the case of the Mo-V-As type catalysts, in view of the fact that arsenic, a highly toxic material, is used, there is the need to exercise caution in handling the spent gas and liquor at the time of the preparation of the catalyst and in carrying out the reaction. Moreover, there is the drawback that the catalytic life of these catalysts is short, which is a disadvantage when using these catalysts for commercial operations. For example, according to a comparative experiment that was carried out by us on the basis of Example 1 of Japanese Patent Publication No. 16604/67, the activity of the Mo-V-As catalyst declined with the passage of time, with the consequence that the yield of acrylic acid, which was 70% at the outset of the reaction, fell to 54.6% after the passage of 500 hours and as low as 44.8% after the passage of 1000 hours.

On the other hand, while some of the known Mo-V type catalysts do demonstrate excellent reaction results, the space velocity of these are generally slow (i.e. 500–1500 hr$^{-1}$). Hence, the productivity of the product (space time yield: STY) is low. As ways of raising the productivity, conceivable are such measures as raising the per-pass yield of the acrylic acid, increasing the concentration of acrolein in the starting feed and/or increasing the space velocity. However, a great improvement cannot be expected by raising the yield of the acrylic acid, since in many of the patents the yield is already as high as 70–90%. Hence, the measures by which a great improvement can be expected in the productivity are that of raising the concentration of the starting arcolein and/or that of increasing the space velocity. However, it is well known that when the concentration of acrolein is raised, the per-pass conversion of acrolein declines to result in a drop in the yield of acrylic acid. On the other hand, as is apparent from Japanese Patent Publication Nos. 24355/72 and 13092/73, when the space velocity is increased (i.e. the contact time is shortened) in the case of the catalysts used in the conventional patents, there is the drawback that the conversion of acrolein as well as yield of acrylic acid declines greatly. Thus, in any of these cases a great improvement in productivity cannot be expected by the use of the conventional catalysts. Furthermore, since the conversion of acrolein falls, the process is burdened in that a great amount of unreacted acrolein must be recycled.

Accordingly, it is an object of this invention to provide a new oxidation catalyst for preparing acrylic acid by the use of which the defects of the conventional oxidation catalysts for acrolein are eliminated, which catalyst not only excels in catalytic activity (namely, the property of providing acrylic acid in good yield at a high selectivity and productivity) but also has a long active life.

This object of the invention can be achieved by using an oxidation catalyst composition having the following empirical formula $$Mo_aP_bV_cL_dM_eO_f$$

wherein L is at least one element selected from the group consisting of Rb, Cs and K; M is at least one element selected from the group consisting of Sr, Nb, Cd, B, Zn and Pb; and a, b, c, d, e and f each represent the number of atoms of each element; the preferred atomic ratio of a:b:c:d:e being in the range of about 12:0.1–8:0.1–8:0.1–8:0–6; and f being the number of oxygen atoms determined by the valence requirements of the other elements present; a more preferred atomic ratio of a:b:c:d:e being in the range of about 12:0.3–5:0.3–5:0.3–5:0–3.

When the invention catalyst contains the M constituent, there is a still greater enhancement of its performance. The results manifested are especially conspicuous when the M constituent is added in an atomic ratio of Mo:M of 1:0.05–6, and preferably 1:0.05–3. Hence, in a catalyst containing M, the mole ratio of a:b:c:d:e is preferably 12:0.1–8:0.1–8:0.1–8:0.05–6, and more preferably 12:0.3–5:0.3–5:0.3–5:0.05–3.

The invention catalyst, an oxide complex of Mo, P, V, L and M, can be used in stably oxidizing acrolein under practical reaction conditions to prepare acrylic acid in a higher yield and selectivity as well as higher productivity than the conventional catalysts. Furthermore, since the catalytic activity can be maintained at a high level for a prolonged period of time, the reaction can be performed continuously over an extended period of time.

In addition, another advantage had by the use of the invention catalyst is that, as compared with the conventional catalysts, the per-pass conversion of acrolein and yield of acrylic acid are high even when the space velocity is fast.

The catalyst may be made, for example, by the evaporative drying method or the coprecipitation method, both of which are well known in the art. The starting constituent elements of the catalyst do not always have to be in the form of an oxide but may be in the form of a metal, metal salt, acid or base so long as they can be converted to the corresponding metal oxides by calcination. Typical examples include salts such as ammonium salts, nitrate or halides; free acids such as molybdic acid or phosphoric acid; heteropolyacids containing molybdenum, such as phosphomolybdic acid, and heteropolyacid salts such as ammonium salt of phosphomolybdic acid. Prior to use, the catalyst composition is preferably calcined for several hours, say, up to fifteen or sixteen hours at about 250°–700° C., preferably about 300°–600° C. more preferably 350°–450° C. in air, a reducing atmosphere or the feed gas.

The catalyst can be prepared, for example, by admixing an aqueous molybdate solution, such as ammonium molybdate, with an aqueous solution containing a vanadium compound, then adding an aqueous solution containing phosphoric acid and an aqueous solution containing a water-soluble compound of an L element, followed, if desired, by further adding an aqueous solution containing a water-soluble compound of an M element, then evaporatively drying the entire mixture with stirring, and thereafter calcining the solid obtained, pulverizing the calcined product, and, if necessary, molding it into a suitable shape. Other examples of the catalyst preparation are described, in the working examples to be given later. Preferably, the catalyst is prepared by mixing the starting compounds so that the constituent elements will form such complex compounds as heteropolyacids, their acid salts or ammonium salts, following which the resulting compound is calcined to produce the corresponding oxides in situ. The so obtained calcined product is pulverized and then molded into pellets, if necessary. Frequently, depending on the raw materials used to manufacture the instant catalyst, calcination temperature and calcination times, the ammonium radical is present as one of the complex components making up the resulting catalyst. A catalyst of this kind can also be used as the catalyst in this invention.

Those skilled in the art can select the desired method of preparing the catalyst. It is not yet clear however, in what state the individual elements of the catalyst composition, including oxygen, are during the reaction when the catalyst is exhibiting its catalytic action.

While the catalyst can be used in the molded or powdered form, it is also possible to use it after dilution with an inert diluent. If desired, the catalyst can be deposited on a suitable inert carrier material. Examples of suitable carriers include alumina, silicon carbide, graphite, inert titania, zirconium oxide, thorium chloride, pumice, silica gel or celite. The amount of the diluent or carrier is not critical since it has no substantial effect on the activity of the catalyst.

The source of molecular oxygen can be pure oxygen or air. Furthermore, it is possible to introduce into the reaction zone an inert diluent gas such as steam, nitrogen, argon, carbon dioxide, helium or a saturated hydrocarbon, for example, methane, ethane or propane.

The concentration of acrolein in the feed gas to be introduced into the reactor is preferably from about 1 to about 25% by volume. On the other hand, the molar ratio of acrolein to molecular oxygen is conveniently about 1: (0.1–25.0), preferably about 1: (0.1–20.0). The reaction temperature is usually in the range of about 300° to 500° C., preferably about 320° to about 450° C., and the reaction pressure can be from a reduced pressure of less than atmospheric pressure to a superatmospheric pressure, say, up to about 15 atms. Preferably, the reaction pressure is about 0.5 to about 10 atmospheres. The contact time (on the basis of 0° C. and 1 atm.) is from about 0.1 to about 20 seconds, preferably about 0.1 to about 15 seconds. The type of reactor with which the catalysts of the present invention may be used may be any of those which are conventional, such as the fluidized, moving or fixed bed type. The reaction product can be recovered by known techniques; for example, condensation and liquefaction by means of a condenser or extraction with water or a suitable solvent.

The invention is illustrated by the following Examples in which the catalysts are used in the conversion of acrolein. The conversion of acrolein, the yield of acrylic acid and the selectivity therefor are defined below. The analysis was carried out by gas chromatography in all cases.

$$\text{Conversion}(\%) = \frac{\text{Acrolein fed(mol)} - \text{Unreacted acrolein(mol)}}{\text{Acrolein fed(mol)}} \times 100$$

$$\text{Yield}(\%) = \frac{\text{Acrylic acid formed(mol)}}{\text{Acrolein fed(mol)}} \times 100$$

$$\text{Selectivity}(\%) = \frac{\text{Yield}}{\text{Conversion}} \times 100$$

The abbreviations used in the tables appearing in the Examples have the following meanings.
Cat. = catalyst
RT = reaction temperature
AL = acrolein
AA = acrylic acid
conv. = conversion
sel. = selectivity.

Furthermore, in the following Examples, the indication of the composition of the catalyst does not specifically refer to the presence of oxygen.

EXAMPLE 1

Ammonium molybdate (212 g) was dissolved in 300 ml. of water with heating. Ammonium metavandate (23.4 g) was dissolved in 200 ml. of a warm aqueous solution of 35.1 g of oxalic acid, and this latter solution was added to the aqueous ammonium molybdate solution prepared above, followed by stirring the mixture. Furthermore, an aqueous solution of 23 g of 85 wt% phosphoric acid in 50 ml. of water and an aqueous solution obtained by dissolving 39.0 g of cesium nitrate ($CsNO_3$) in 200 ml. of water with heating were added to the mixture, and the entire mixture was evaporated to dryness with stirring. The solid obtained was calcined at 430° C. for 16 hours in a muffle furnace, pulverized, and screened to a screen size of 4 to 8 mesh (Tyler No. 4–No. 8, 4.00 mm–2.38 mm).

The atomic ratio of Mo:P:V:Cs of the resulting catalyst composition (Cat. No. 1) was 12:2:1:2.

Catalysts indicated in Table 1 were prepared in the same way but using 20.2 g of potassium nitrate ($KNO_3$), and 29.5 g of rubidium nitrate ($RbNO_3$) severally, instead of the cesium nitrate ($CsNO_3$). Comparison catalysts indicated in Table 1 were also prepared in the same way.

A stainless steel reaction tube 2.5 cm in inside diameter and 60 cm in length was packed with 100 ml. of the catalyst, and heated by a molten metal bath. A feed gas having an acrolein:$O_2$:$N_2$:$H_2O$ molar ratio of 1:1.5:8:9.5 was passed through the reaction tube while the contact time was adjusted to 1.2 seconds (on the basis of 0° C., and 1 atm.). The results obtained are shown in Table 1.

The reaction temperatures shown in Table 1 are the maximum temperatures of the catalyst layer at which the best results were obtained.

The results shown in Table 1 demonstrate that, in spite of the short contact time, the catalysts of the present invention give acrylic acid in high selectivity and yield. It is also shown by these results that acrylic acid is obtained in excellent space time yield when the catalysts of this invention are used.

Table 1

| Run No. | Cat. No. | Catalyst composition (atomic ratio) | RT (°C.) | Al conv. (%) | AA Yield (Sel.) (%) |
|---|---|---|---|---|---|
| | | This invention | | | |
| I-1 | 1 | $Mo_{12}P_2V_1Cs_2$ | 405 | 91.4 | 82.3 (90.0) |
| I-2 | 2 | $Mo_{12}P_2V_1K_2$ | 411 | 86.0 | 70.9 (82.4) |
| I-3 | 3 | $Mo_{12}P_2V_1Rb_2$ | 408 | 86.7 | 72.5 (83.6) |
| | | Comparison | | | |
| I-4 | C-1 | $Mo_{12}P_2V_1$ | 420 | 54.3 | 39.3 (72.4) |
| I-5 | C-2 | $Mo_{12}P_2Cs_2$ | 418 | 58.9 | 44.4 (75.4) |
| I-6 | C-3 | $Mo_{12}P_2K_2$ | 423 | 51.6 | 33.4 (64.7) |
| I-7 | C-4 | $Mo_{12}P_2Rb_2$ | 420 | 55.8 | 39.2 (70.3) |
| I-8 | C-5 | $Mo_{12}P_2Tl_2$ | 421 | 57.8 | 45.6 (78.9) |
| I-9 | C-6 | $Mo_{12}V_1Tl_2$ | 425 | 55.2 | 11.9 (21.6) |
| I-10 | C-7 | $Mo_{12}V_1Cs_2$ | 420 | 57.3 | 13.2 (23.0) |
| I-11 | C-8 | $Mo_{12}V_1K_2$ | 422 | 41.0 | 8.5 (20.7) |
| I-12 | C-9 | $Mo_{12}V_1Rb_2$ | 420 | 44.3 | 9.2 (20.8) |

EXAMPLE 2

The procedure of Example 1 was repeated to prepare the catalysts shown in Table 2, and the same reaction as that of Example 1 was performed. The results obtained are shown in Table 2.

Table 2

| Run No. | Cat. No. | Catalyst composition (atomic ratio) | RT (°C.) | AL conv. (%) | AA Yield (Sel.) (%) |
|---|---|---|---|---|---|
| II-1 | 5 | $Mo_{12}P_2V_{0.5}Cs_2$ | 408 | 87.3 | 77.3 (88.5) |
| II-2 | 5 | $Mo_{12}P_2V_2Cs_2$ | 411 | 93.7 | 75.1 (80.1) |
| II-3 | 7 | $Mo_{12}P_2V_1Cs_1$ | 402 | 94.1 | 77.4 (82.3) |
| II-4 | 8 | $Mo_{12}P_1V_1Cs_{0.5}$ | 381 | 91.5 | 69.8 (76.3) |
| II-5 | 9 | $Mo_{12}P_{0.5}V_{1.5}Cs_1$ | 385 | 90.0 | 71.7 (70.7) |
| II-6 | 10 | $Mo_{12}P_3V_1Cs_2$ | 410 | 85.2 | 73.7 (86.5) |
| II-7 | 11 | $Mo_{12}P_2V_{0.5}K_1$ | 410 | 84.9 | 68.2 (80.3) |
| II-8 | 12 | $Mo_{12}P_1V_1K_{0.5}$ | 385 | 82.3 | 64.4 (78.3) |
| II-9 | 13 | $Mo_{12}P_2V_{0.5}Rb_1$ | 406 | 82.6 | 66.7 (80.8) |
| II-10 | 14 | $Mo_{12}P_1V_1Rb_{0.5}$ | 391 | 84.0 | 63.0 (75.0) |
| II-11 | 15 | $Mo_{12}P_2V_{0.5}Tl_2$ | 410 | 85.3 | 74.7 (87.6) |
| II-12 | 18 | $Mo_{12}P_2Cs_1Rb_1V_1$ | 408 | 88.8 | 76.4 (86.0) |
| II-13 | 19 | $Mo_{12}P_2Cs_1Tl_1V_1$ | 403 | 92.7 | 83.4 (90.0) |

EXAMPLE 3

Ammonium molybdate (212 g) was dissolved in 300 ml. of water with heating. Ammonium metavanadate (23.4 g) was dissolved in 200 ml. of a warm aqueous solution of 35.1 g of oxalic acid, and the latter solution was added to the aqueous ammonium molybdate solution prepared above, followed by stirring the mixture. Furthermore, an aqueous solution of 23 g of 35 wt.% phosphoric acid in 50 ml. of water, an aqueous solution obtained by dissolving 39.0 g of cesium nitrate ($CsNO_3$) in 200 ml. of water with heating, and an aqueous solution of 10.55 g of strontium nitrate [$Sr(NO_3)_2$] in 200 ml. of water were added to the mixture, and the entire mixture was evaporated to dryness with stirring. The solid obtained was calcined at 430° C. for 16 hours in a muffle furnace, pulverized, and screened to a screen size of 4 to 8 mesh (Tyler No. 4–No. 8, 4.00 mm–2.38 mm).

The atomic ratio of Mo:P:V:Cs:Sr of the resulting catalyst composition (Cat. No. 20) was 12:2:1:2:0.5.

In similar manner, the components were varied as in (i) and (ii), below, to prepare the catalysts shown in Table 3.

(i) Instead of $CsNO_3$, 20.2 g of $KNO_3$, and 29.5 g of $RbNO_3$ were severally used.

(ii) Instead of $Sr(NO_3)_2$, 13.45 g of $Nb(HC_2O_4)_5$, 1.52 g of $(NH_4)_2CrO_4$, 7.7 g of $Cd(NO_3)_2.4H_2O$, 3.1 g of $H_3BO_3$, 7.43 g of $Zn(NO_3)_2.6H_2O$ and 16.55 g of $Pb(NO_3)_2$ were severally used.

Table 3

| Run No. | Cat. No. | Catalyst composition (atomic ratio) | RT (°C.) | AL conv. (%) | AA yield (sel.) (%) |
|---|---|---|---|---|---|
| III-1 | 20 | $Mo_{12}P_2V_1Cs_2Sr_{0.5}$ | 405 | 93.8 | 83.5 (89.0) |
| III-2 | 21 | $Mo_{12}P_2V_1Cs_2B_{0.5}$ | 416 | 94.5 | 89.0 (94.2) |
| III-3 | 22 | $Mo_{12}P_2V_1Cs_2Cd_{0.25}$ | 408 | 95.0 | 87.4 (92.0) |
| III-4 | 23 | $Mo_{12}P_2V_1K_2Nb_{0.25}$ | 408 | 91.1 | 78.8 (85.5) |
| III-5 | 24 | $Mo_{12}P_2V_1Rb_2Sr_{0.5}$ | 410 | 89.8 | 78.3 (87.2) |
| III-6 | 25 | $Mo_{12}P_2V_1Tl_2Zn_{0.25}$ | 410 | 95.2 | 86.7 (91.1) |
| III-7 | 26 | $Mo_{12}P_2V_1Tl_2Pb_{0.5}$ | 415 | 95.8 | 86.9 (90.7) |

EXAMPLE 4

Acrolein was oxidized continuously for prolonged periods of time under the same conditions as in Example 1 using each of the catalysts shown in Table 4 which were obtained in Examples 1 and 3. The performance of each catalyst used after a lapse of 30 days from the initation of the reaction is shown in Table 5. The temperature of the molten metal bath was kept almost constant during the reaction. In the table, the "O" in the column entitled "time that elapsed" means the initial stage of the reaction. It can be seen from Table 4 that the catalysts prepared according to the present invention do not lose their activity even after a lapse of a long period of time and prove to be excellent catalysts having a very long active life. On the other hand, the activity of the comparison catalysts decreases abruptly within a short period of time, and therefore, their active life was short.

Table 4

| Run No. | Cat. No. | Catalyst composition (atomic ratio) | Time that elapsed (days) | RT (°C.) | AL conv. (%) | AA Yield (Sel.) (%) |
|---|---|---|---|---|---|---|
| | | This invention | | | | |
| TV-1 | 1 | $Mo_{12}P_2V_1Cs_2$ | 0 | 405 | 91.4 | 82.3 (90.0) |
| | | | 30 | 402 | 90.0 | 83.1 (92.3) |
| | | | 0 | 411 | 86.0 | 70.9 (8.4) |

Table 4-continued

| Run No. | Cat. No. | Catalyst composition (atomic ratio) | Time that elapsed (days) | RT (°C.) | AL conv. (%) | AA Yield (Sel.) (%) |
|---|---|---|---|---|---|---|
| IV-2 | 2 | $Mo_{12}P_2V_1K_2$ | 30 | 410 | 84.3 | 70.9 (84.1) |
| | | | 0 | 408 | 86.7 | 72.5 (83.6) |
| IV-3 | 3 | $Mo_{12}P_2V_1Rb_2$ | 30 | 407 | 85.8 | 72.5 (84.5) |
| | | | 0 | 416 | 94.5 | 89.0 (94.2) |
| IV-4 | 21 | $Mo_{12}P_2V_1Cs_2B_{0.5}$ | 30 | 415 | 94.5 | 89.5 (94.7) |
| | | | 0 | 408 | 91.1 | 78.8 (86.5) |
| IV-5 | 23 | $Mo_{12}P_2V_1K_2Nb_{0.25}$ | 30 | 405 | 90.0 | 79.2 (88.0) |
| | | Comparison | | | | |
| | | | 0 | 420 | 54.3 | 39.3 (72.4) |
| IV-7 | C-1 | $Mo_{12}P_2V_1$ | 30 | 415 | 30.1 | 21.7 (72.1) |
| | | | 0 | 418 | 58.9 | 44.4 (75.4) |
| IV-8 | C-2 | $Mo_{12}P_2Cs_2$ | 30 | 411 | 32.6 | 25.0 (76.6) |
| | | | 0 | 425 | 55.2 | 11.9 (21.6) |
| IV-9 | C-7 | $Mo_{12}V_1Tl_2$ | 30 | 418 | 36.8 | 8.6 (23.3) |
| | | | 0 | 420 | 57.3 | 13.2 (23.0) |
| IV-10 | C-8 | $Mo_{12}V_1Cs_2$ | 30 | 413 | 31.5 | 7.9 (25.1) |

We claim:

1. A process for the preparation of acrylic acid which comprises reacting acrolein with molecular oxygen in the vapor phase in the presence of an oxidation catalyst composition having the following empirical formula $$Mo_aP_bV_cL_dM_eO_f$$

wherein L is at least one element selected from the group consisting of Rb, Cs and K; M is at least one element selected from the group consisting of Sr, Nb, Cd, B, Zn and Pb; and a, b, c, d, e and f each represent the number of atoms of each element; the atomic ratio of a:b:c:d:e being 12:0.1–8:0.1–8:0.1–8:0–6; and f being the number of oxygen atoms determined by the valence requirements of the other elements present.

2. The process of claim 1, which comprises carrying out the reaction at a temperature of 300° to 500° C.

3. The process of claim 1 wherein the source of said molecular oxygen is air.

4. The process of claim 1 wherein an inert diluent gas is introduced into the reaction zone.

5. The process of claim 1 wherein the catalyst is diluted with an inert diluent or supported on an inert carrier.

6. The process of claim 1 wherein the atomic ratio of a:b:c:d:e is 12:0.3–5:0.3–5:0.3–5:0–3.

7. The process of claim 1 wherein the atomic ratio of a:b:c:d:e is 12:0.3–5:0.3–5:0.3–5:0.05–3.

8. The process of claim 1 wherein L is Rb.

9. The process of claim 1 wherein L is Cs.

10. The process of claim 1 wherein L is K.

11. A process for the preparation of acrylic acid which comprises reacting acrolein with molecular oxygen in the vapor phase in the presence of an oxidation catalyst composition having the following empirical formula $$Mo_aP_bV_cL_dM_eO_f$$

wherein L is at least one element selected from the group consisting of Rb, Cs and K; M is at least one element selected from the group consisting of Sr, Zn and Cd; and a, b, c, d, e and f each represent the number of atoms of each element; the atomic ratio of a:b:c:d:e being 12:0.3–5:0.3–5:0.3–5:0.05–3; and f being the number of oxygen atoms determined by the valence requirements of the other elements present.

12. The process of claim 11 wherein M is Sr.

13. The process of claim 11 wherein M is Zn.

14. The process of claim 11 wherein M is Cd.

* * * * *